United States Patent [19]

Wickham

[11] Patent Number: 5,702,425
[45] Date of Patent: Dec. 30, 1997

[54] APPARATUS AND METHOD OF NOISE CLASSIFICATION IN AN IMPLANTABLE CARDIAC DEVICE

[75] Inventor: Peter John Wickham, Fivedock, Australia

[73] Assignee: Pacesetter, Inc., Sylmar, Calif.

[21] Appl. No.: 700,730

[22] Filed: Aug. 13, 1996

[51] Int. Cl.⁶ ........................................ A61N 1/362
[52] U.S. Cl. ........................ 607/9; 607/25; 128/703
[58] Field of Search .................. 607/9, 25; 128/702, 128/703, 704

[56] References Cited

U.S. PATENT DOCUMENTS

| | | | |
|---|---|---|---|
| 4,261,370 | 4/1981 | von Nettelhorst | 128/702 |
| 4,516,579 | 5/1985 | Irnich | 607/9 |
| 4,649,931 | 3/1987 | Beck . | |
| 4,796,638 | 1/1989 | Sasaki | 128/704 |
| 4,960,123 | 10/1990 | Maker | 128/702 |
| 5,209,229 | 5/1993 | Gilli . | |
| 5,265,601 | 11/1993 | Mehra . | |
| 5,280,792 | 1/1994 | Leong et al. | 128/702 |
| 5,395,393 | 3/1995 | Wickham | 607/9 |
| 5,560,369 | 10/1996 | McClure et al. . | |
| 5,620,466 | 4/1997 | Haefner et al. . | |

Primary Examiner—William E. Kamm
Assistant Examiner—Carl H. Layno
Attorney, Agent, or Firm—Gottlieb, Rackman & Reisman

[57] ABSTRACT

An implantable cardiac device includes electrodes for sensing and pacing the heart, and optionally, defibrillation electrodes. The IECG sensed in the heart is processed to derive raw sense signals indicative of whether the sensed QRS complexes exceed a predetermined range. These signals are used to control the pacing pulses, and to detect high amplitude noise. This noise is differentiated from tachycardia.

11 Claims, 9 Drawing Sheets

APPARATUS AND METHOD OF NOISE CLASSIFICATION IN AN IMPLANTABLE CARDIAC DEVICE

BACKGROUND OF THE INVENTION

A. Field of Invention

This invention pertains to implantable cardiac devices (ICDs) such as pacemakers, and more particularly to such devices with means for distinguishing ambient electronic noise from arrhythmic cardiac behavior such as abnormally fast heart beats so as to provide appropriate and reliable therapy to a patient even in the presence of electrical interference.

B. Description of the Prior Art

Typically ICDs monitor a patient's heart condition by sensing the Intra Cardiac Electrogram (IECG), a voltage that occurs when the cardiac muscle depolarizes at the beginning of each heart contraction. The IECG is sensed by one or two electrodes placed in or near the heart, where it appears as a voltage waveform which is normally referred to as the QRS complex. The IECG QRS complex during normal heart beats has an amplitude of about 15 to 25 mV and a broad frequency spectrum in the range of about 40 to 70 Hz. There are numerous systems in the prior art that detect the QRS complex by amplifying the IECG signal, filtering it to reduce noise and then detecting the QRS complex with an amplitude threshold detector. The threshold detector may have a fixed threshold or adapt the threshold to the changing amplitude of the signal.

A problem with this method of detecting cardiac activity is that because of its low amplitude and particular spectral characteristics, the IECG can be corrupted by ambient signals such as noise or artefact from natural and artificial sources. Common sources of such ambient signals include electromyographic noise from skeletal muscles near the electrodes, contact noise from intermittent contact in the electrode circuit (either the electrode wiring or between the electrode and heart muscle as the heart moves) and radiated or induced voltages from voltage lines and other external power sources. These ambient signals appear as waveforms with an amplitude and frequency content similar to the QRS complex and thus may confuse the sensing system of the ICD and cause incorrect therapy to be applied to the patient. This problem is compounded by the nature of the IECG of some arrhythmias, in particular, ventricular fibrillation, which has a lower amplitude (0.2 to 5 Mv), higher rate (300 to 400 beats/min.) and lower frequency content than the normal IECG.

A common method used in many pacemakers to resolve this problem is referred to as the noise sensing window. This method takes advantage of the fact that even the fastest natural heart rates result in signals which follow a QRS complex by at least 300–400 ms. Accordingly a noise window is designated as a window typically 100–120 ms after a QRS complex is sensed. Any signals sensed in this window is assumed to be noise.

A variation of this method is described in U.S. Pat. No. 4,173,230 to Digby entitled "Noise Elimination and Refractory Period Control In Demand Pacemakers" where a combination of filters and refractory periods are used to reduce the effect of noise.

Another noise detection method is described in U.S. Pat. No. 4,649,931 to Beck entitled "Sampled Data Sense Amplifier". The device disclosed therein searches for discontinuities in the background level of the sensed signal, and therefore ignores any noise if it is continuous and uniform.

U.S. Pat. No. 5,395,393 discloses a noise elimination method using variable amplifier thresholds.

These prior art noise detection systems have inherent problems of their own. One such problem exists if the noise level is near the detection threshold, or is of variable amplitude. In this situation, the detection is intermittent, thus providing a variable classification of noise that may lead to intermittent or indeterminate delivery of therapy to the patient. Additionally, these systems fail to work effectively when used for arrhythmia detection where an arrhythmia may be of sufficiently high rate to cause a valid detection to fall in the noise window.

The problem of these systems misclassifying ventricular fibrillation (VF) as noise is significant. This is because the IECG for VF is highly variable and can have short intervals that have very similar characteristics to sine waves induced of by conventional power lines. This is of major consequence to patients with ICDs which require fast and accurate diagnosis of VF for the ICD to effectively save their lives from this lethal arrhythmia.

OBJECTIVES AND SUMMARY OF THE INVENTION

It is an object of the present invention to provide a pacemaker with means for reliably detecting noise before said noise is interpreted erroneously as a tachycardia.

It is another objective of the present invention to provide reliable and unambiguous identification of noise when an IECG signal is contaminated with noise by a method that is not affected by (independent of) high heart rates.

Furthermore, an important feature of the invention is the capability of reliably identifying noise by means of a detection system which is not constrained by the long refractory periods so that a greater number of detect events can be processed and used to provide a more accurate classification of noise.

It is a further objective of this invention to add features to the QRS detection system that allow the presence of these interferences to be identified reliably so that the implant may deliver correct therapy to the patient in the presence of this interference.

Other objectives and advantages of the invention shall become apparent from the following description. This invention is preferably incorporated into an ICD having a threshold sensing systems that automatically adjust the threshold to adapt to different signal amplitudes, for example as disclosed in U.S. Pat. No. 5,395,393. More particularly, an ICD constructed in accordance with this invention includes means for sensing cardiac activity in a patient's heart to generate an input signal, means for defining a range for the input signal, means for generating a noise signal dependent on excursions of said input signal outside said range and control means for generating any signal in accordance with said noise signal. More particularly, the noise generating means generates a pulse for said excursion outside said range. Pulses having a pre-determined period and spacing are defined as pulse trains. Short pulse trains separated by long idle periods identify normal cardiac activity with no noise. Long pulse trains with short idle periods identify normal cardiac operator with noise present. Short pulse trains with short idle periods identify tachycardia.

DETAILED DESCRIPTION OF THE INVENTION

Figure 1:
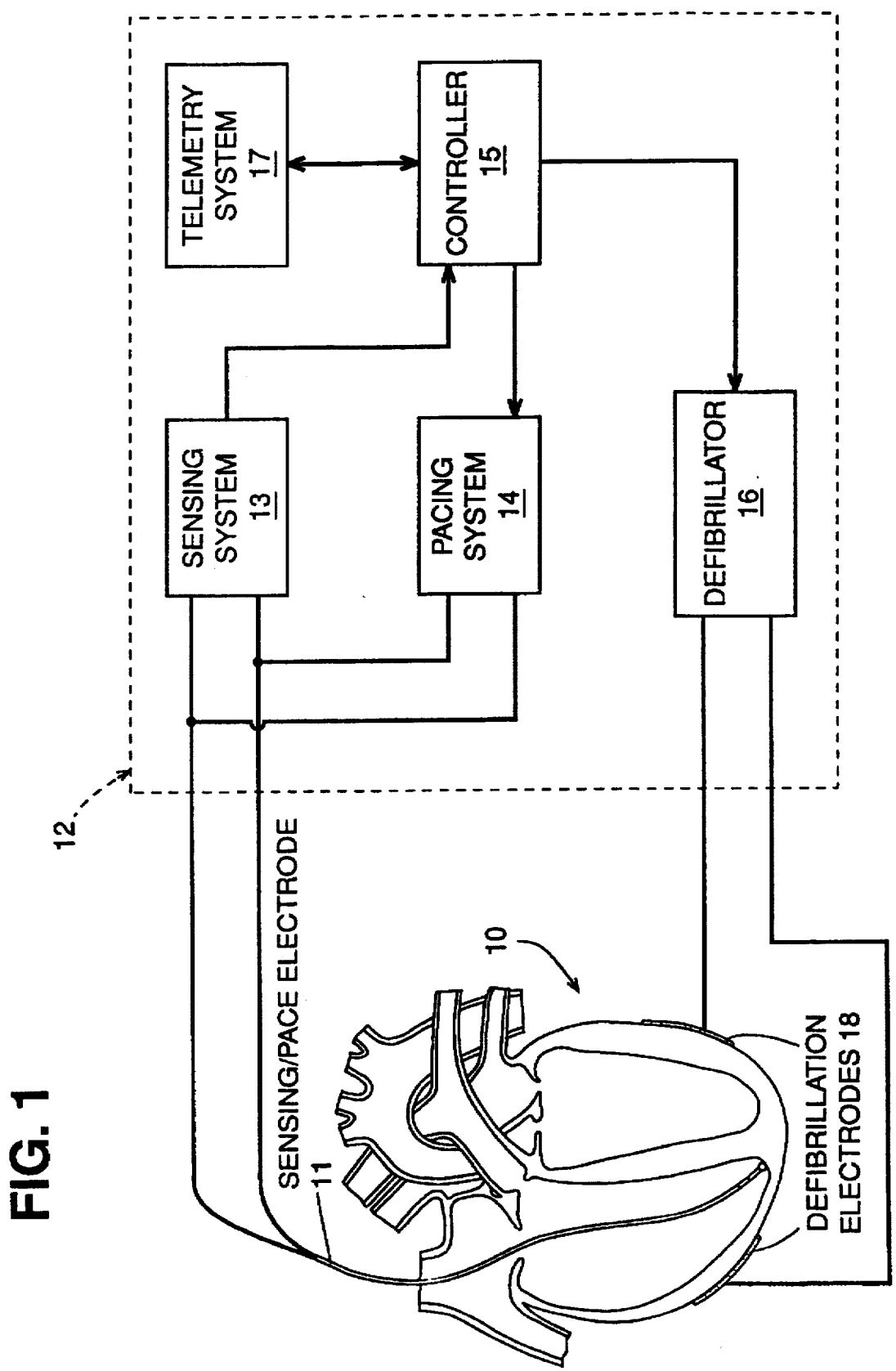
FIG. 1 is a block diagram of an arrhythmia control system in an ICD constructed in accordance with the present invention.

Referring to FIG. 1, there is depicted a block diagram of an ICD device 12 which comprises a cardiac sense/pace leads 11 connected to the patient's heart 10. The intracardiac electrogram signal (IECG) sensed on one of the lead 11 is processed by the sensing system 13 to identify valid cardiac contractions. The sensing system 13 is further adapted to sense when the IECG is noisy, as described in more detail below.

A controller 15 analyses the signals from the sensing system 13 to derive the patient's heart rate. The controller compares this heart rate with criteria selected by the physician to decide whether the heart is experiencing a normal sinus rhythm (NSR), ventricular tachycardia (VT) or ventricular fibrillation (VF). Depending on this determination, the controller 15 can automatically determine whether the patient's heart is in arrhythmia and if so, select an appropriate therapy. For therapy, the controller can cause conventional cardiac pacing pulses to be delivered to the heart from the pacing system 14 and the sense/pace leads 11, or deliver cardioversion or defibrillation shock therapy via the leads 11 or a defibrillator system 16 and the defibrillation electrodes 18. The ICD device 12 can be interrogated and adjusted by radio via the telemetry system 17. Importantly, as previously mentioned, the controller 15 receives an indication about whether a particular sensed waveform is a valid waveform, by analyzing its shape. Moreover, sequential waveforms are further analyzed by the sensing system to identify noise on the electrodes 11. The controller 15 uses these signals to reject waveforms which are invalid because of their shape, or have been identified as noise.

Figure 2:
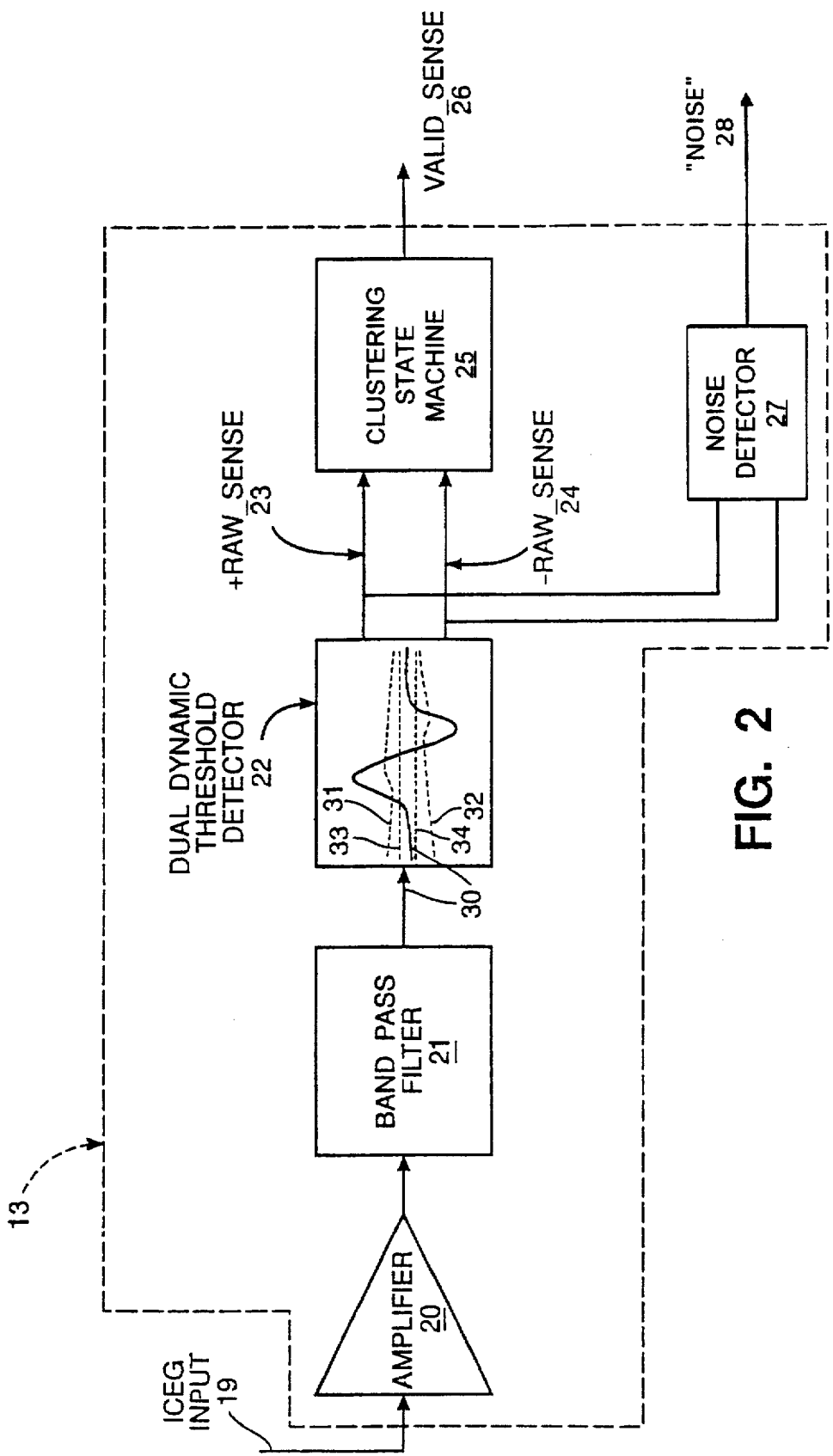
FIG. 2 is a block diagram of the sensing system of FIG. 1.

Referring to FIG. 2, there is shown a block diagram of the sensing system 13 of FIG. 1 which comprises an amplifier (20) which amplifies the IECG received on input 19 to an appropriate level for the following stages. The amplified signal is then passed through a band pass filter 21 to remove high and low frequency noise and artefacts. The filtered QRS input signal 30 is passed to a dual dynamic threshold detector 22. This detector 22 has two independent voltage thresholds and produces a digital "+Raw-sense" output 23 when the signal is greater than a positive threshold, and a −Raw-sense 24 output when the signal is less than a negative threshold.

The +Raw-sense and −Raw-sense signals are passed to a clustering state machine 25 for rationalization. The sampling rate of the system is selected so that typically, each QRS complex in the IECG results in between 2 and 10 raw samples. The clustering state machine 25 analyses these samples and produces a valid-sense (26) output per heart beat if it finds the QRS complex acceptable, as discussed more fully below. The +Raw-sense and −Raw-sense signals are also fed to noise detector 27. If this detector makes a determination that the QRS complex is noisy than it generates a NOISE output on line 27, as discussed below.

Figure 3:
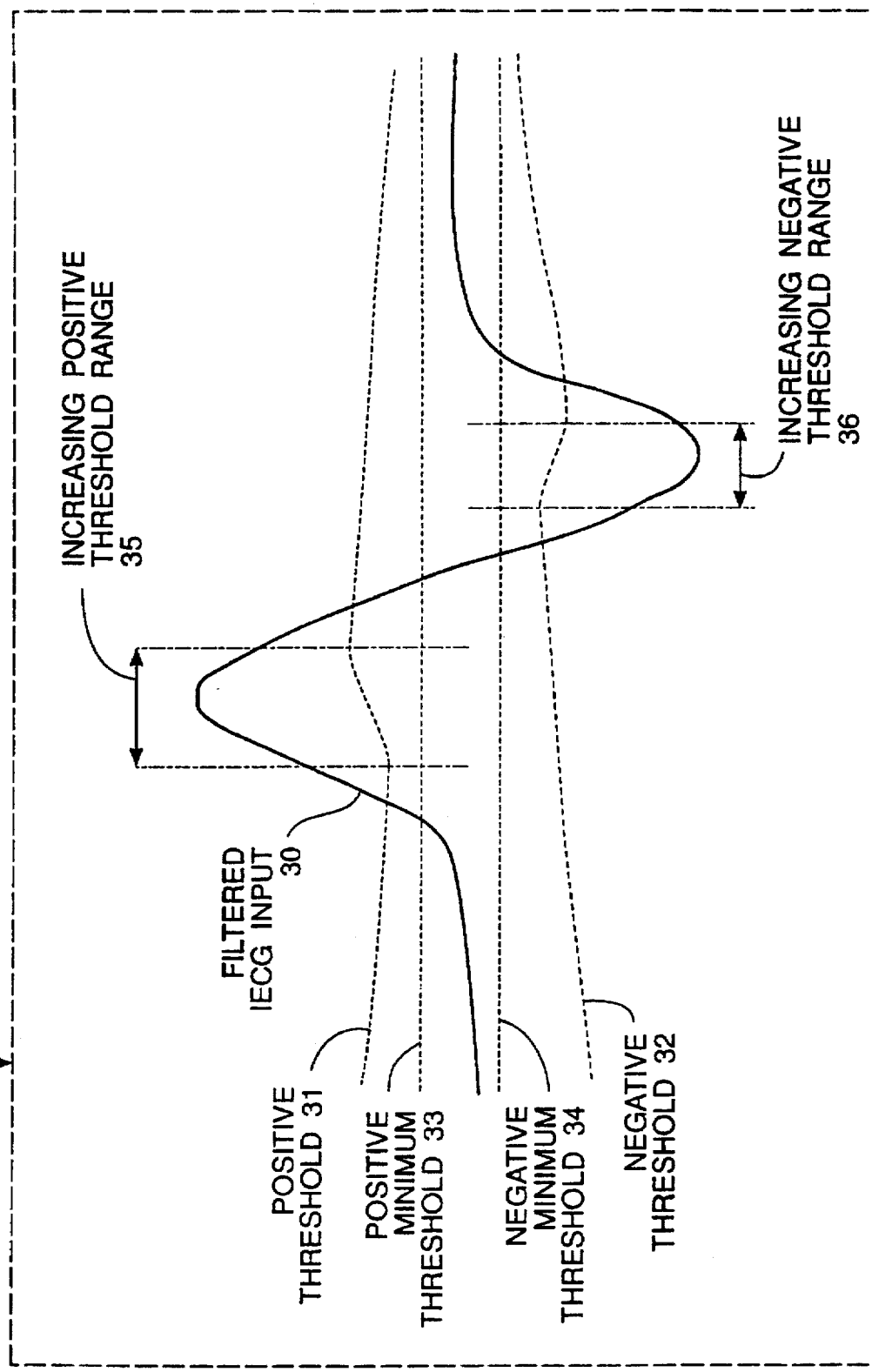
FIG. 3 shows details of the behavior of the two dynamic thresholds derived in the apparatus of FIGS. 1 and 2.

Details of the detector 22 are found in U.S. Pat. No. 5,395,393. Briefly, as shown in FIG. 3, when the positive threshold 31 is greater than half the input signal 30, the threshold 31 decays exponentially towards the positive threshold minimum 33 with a time constant of approx 0.75 seconds. When the positive threshold 31 is less than half the input signal 30, the positive threshold 31 follows up to half the input signal with a shorter time constant of 0.05 secs. The +Raw-sense output is digital signal generated whenever the input signal 30 exceeds the positive threshold 31.

The operation of the negative threshold 32 is a mirror image of that of the positive threshold 31.

Both thresholds have upper limits in that the positive threshold 31 cannot exceed a maximum value (in the preferred embodiment this value is 10 to 20 times the minimum threshold 33), and similarly, the negative threshold 32 cannot exceed a maximum (absolute) value related to the minimum negative threshold 34.

Figure 4:
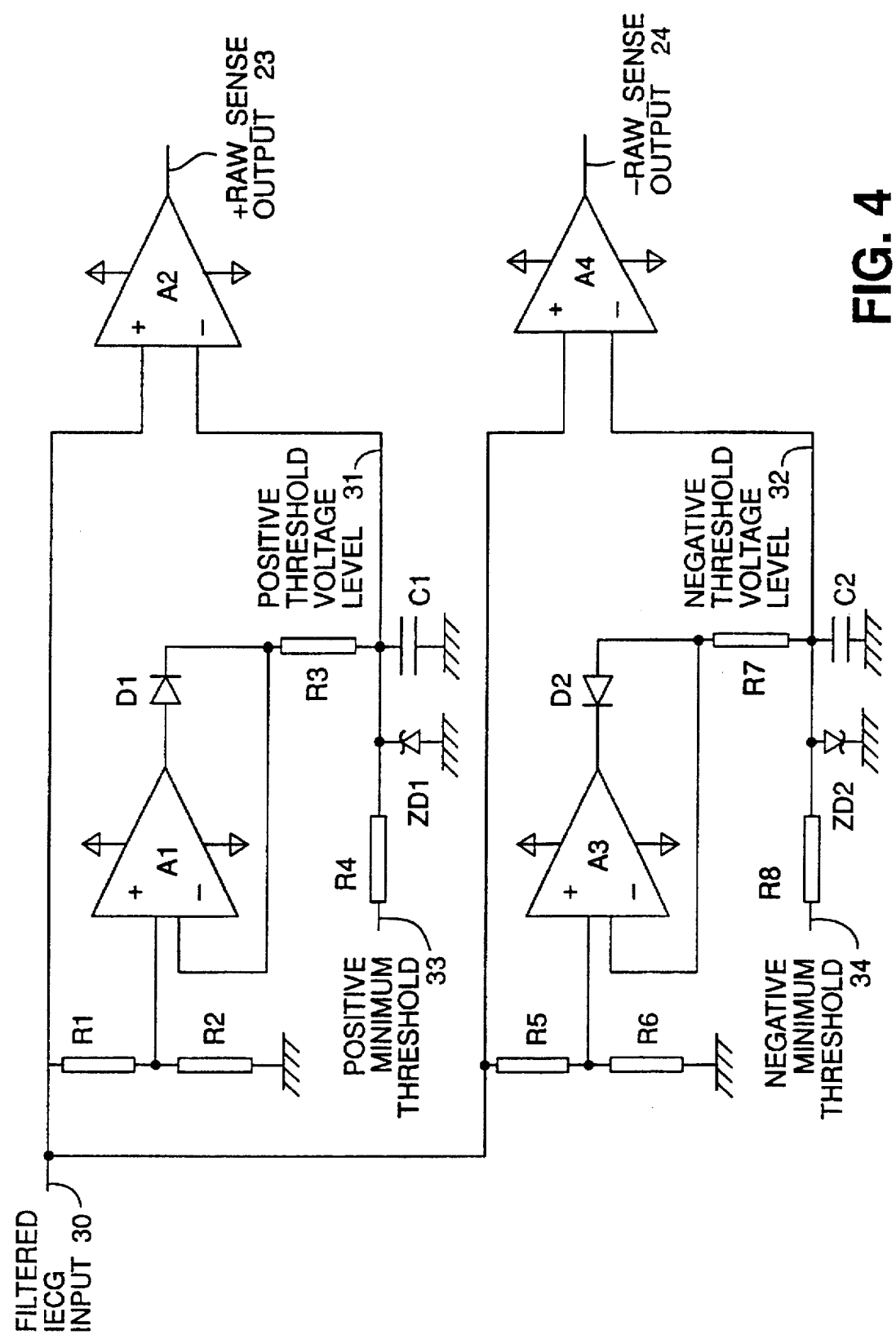
FIG. 4 shows details of a circuit to implement the two dynamic thresholds.

Referring to FIG. 4, there is depicted a circuit disclosed in U.S. Pat. No. 5,395,393 to implement the dual dynamic threshold function. The positive threshold 31 is stored by capacitor C1. When the input 30 exceeds this voltage, the output of amplifier A2 goes high to output a +Raw-sense 41. When half the input voltage is less than the threshold 31, the voltage on C1 is discharged exponentially through r4 towards +Thresh min. 33, a voltage which sets the minimum threshold. Resistors R1 and R2 provide half the input voltage of signal 30 to the precision rectifier formed by A1 and D1 When half the input voltage 30 exceeds the voltage 31 on C1, capacitor C1 is charged up to this new value through resistor R3 with a time constant of 0.05 secs.

The −Raw-sense output 44 is provided by a mirror image arrangement of the above circuit consisting of amplifiers A3 and A4 and associated components.

Figure 5:
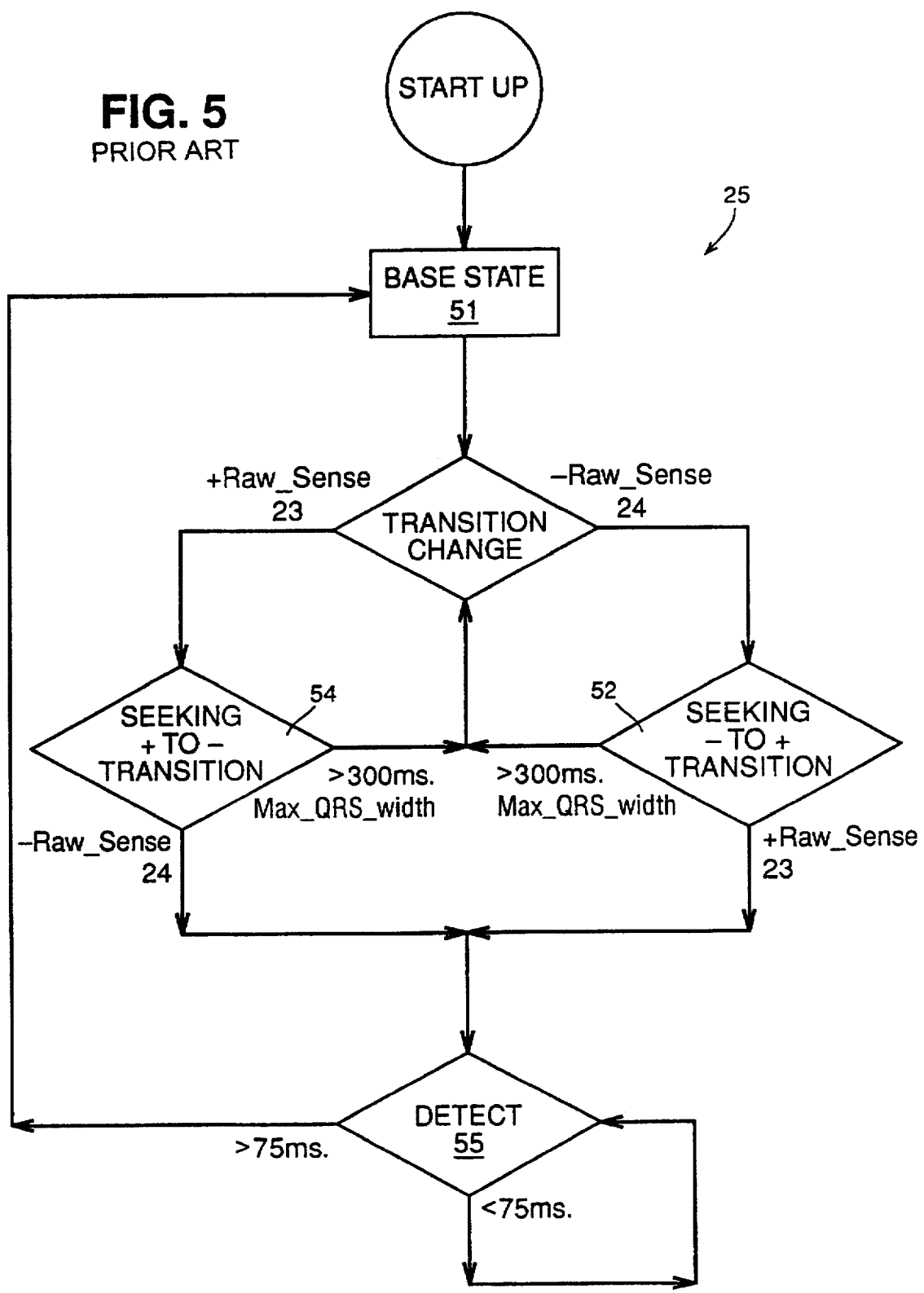
FIG. 5 shows details of a state transition diagram for the clustering state machine.

Referring to FIG. 5, there is depicted the operation of the clustering state machine 25 in FIG. 2 in state transition diagram format. On start up, the state machine 25 commences operation in the base state 51. If a −Raw-detect is received from the dual threshold detector 22, the state machine 25 changes to the seeking − to + transition state 52. If a +Raw-detect signal is received, the state machine changes to the seeking + to − transition state 54. If the state machine 25 spends more than 300 ms in either the seeking − to + transition or seeking + to − transition states, the state machine reverts to the base state 51.

If the state machine is in the seeking − to + transition state 52 and a +Raw-detect is received, the state machine 25 will change to the detect state 55 and at this point, a valid-sense output 26 is generated. This signal indicates to the controller 15 that the QRS complex has been recognized by the sensing system 13 as a proper signal and can be processed to generate therapy for the heart (if any is required).

Similarly, if the state machine is in the seeking + to − transition state 54 and a −Raw-detect is received, the state machine 25 changes to the detect state 55 and generate a valid-sense signal 26.

The state machine 25 remains in the detect state 55 for 75 ms then reverts to the base state 51.

An important feature of the state machine 25 is that valid-sense signal 26 generated by a transition from triggering one threshold to the other threshold within a time window, which is in the range of 300 ms in the preferred embodiment.

The advantage gained by the clustering state machine is that with the filters described, Large T waves often cause raw senses but are unlikely to generate two raw senses of opposite polarities within 300 ms as the majority of T waves have a duration of greater than 300 ms.

The clustering state machine 25 can be implemented by using discrete electronic logic or as a computer program that can be part of the controller 15 for the implantable defibrillator in FIG. 1.

Noise Detection:

Briefly, in the present device, a separate short absolute refractory period is set and used for detecting noise. This period can be in the range of 10–40 ms. Intervals less than the noise detection period are defined and potential noise signals are processed separately from the QRS complex. When a pre-selected consecutive number (i.e., 20) of these noise signals is sensed, a signal is generated to indicate that noise is being sensed.

Figure 5A:
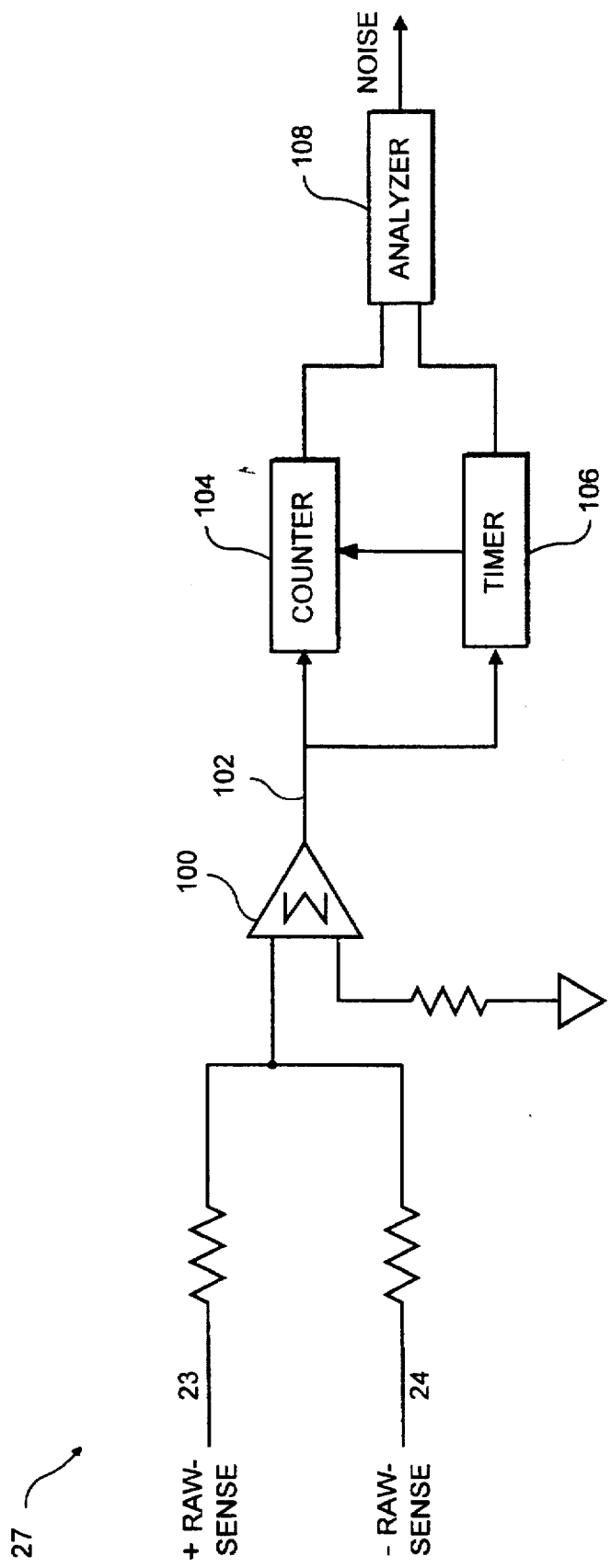
FIG. 5A shows a block diagram for the noise detector in accordance with this invention.

From FIG. 2 it can be seen that the noise detector 27 is a separate sub-system that takes the raw sense information from the dual threshold detector 22, processes this independently from the clustering state machine 25 and produces a NOISE signal to indicate to the controller 15 that the patient's IECG is contaminated with the artefacts as described above. More particularly, as shown in FIG. 5A, the noise detector 27 includes an OR gate 100 receiving the two RAW SENSE signals on lines 23 and 24. The combined signal is output by the OR gate on line 102 to a pulse counter 104, a timer 106 and an analyzer 108. In operation, the signal on line 102 is a pulse train that is the sum of the output of both positive and negative threshold detectors.

The timer 106 measures the time interval between each of these pulses with the counter 104 counting the number of consecutive intervals that are shorter than the 'Noise detect interval' (typically 20 to 50 ms).

Figure 6:
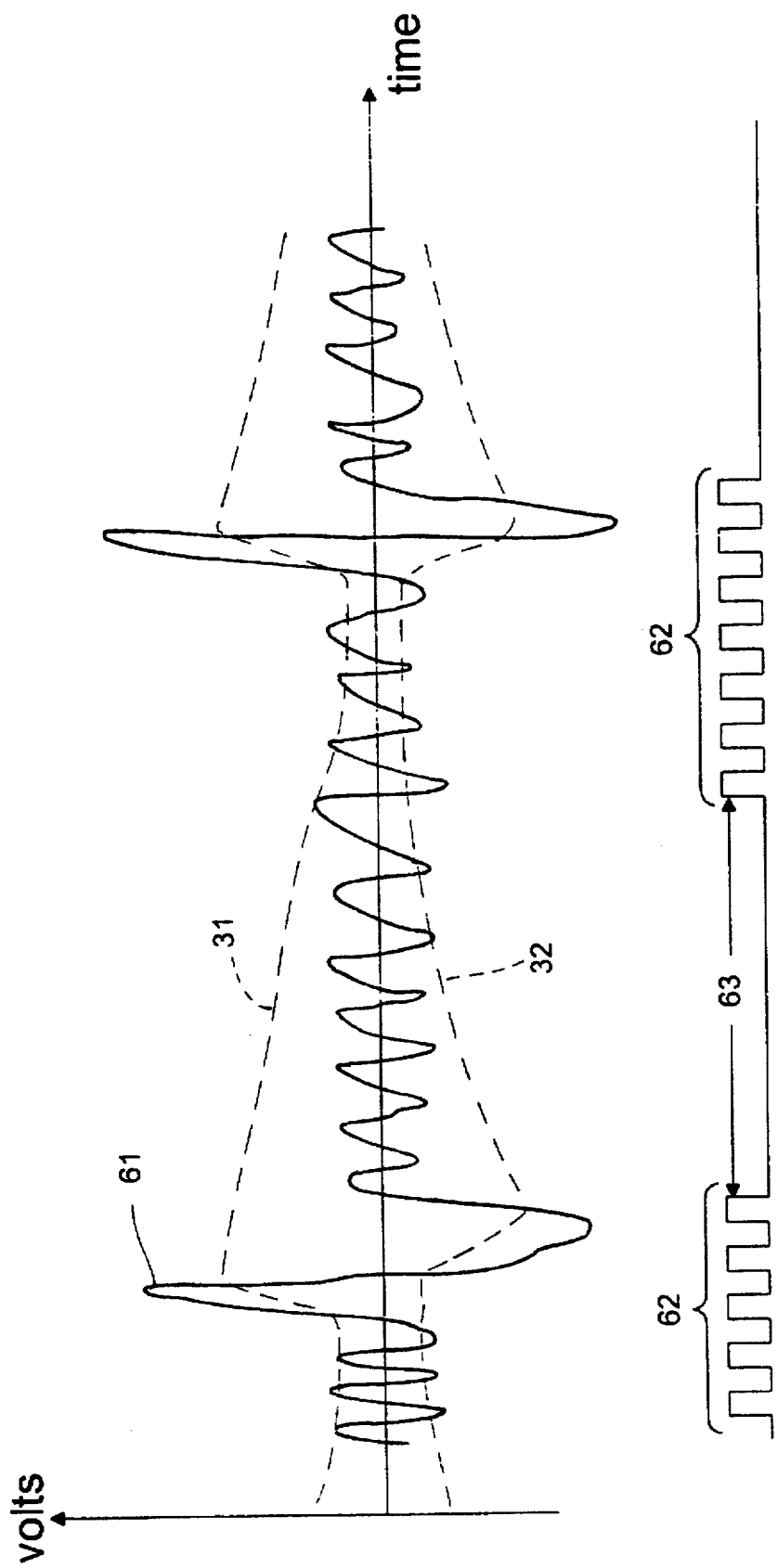
FIG. 6 shows details of the operation of the noise detector with low amplitude of noise.
Figure 7:
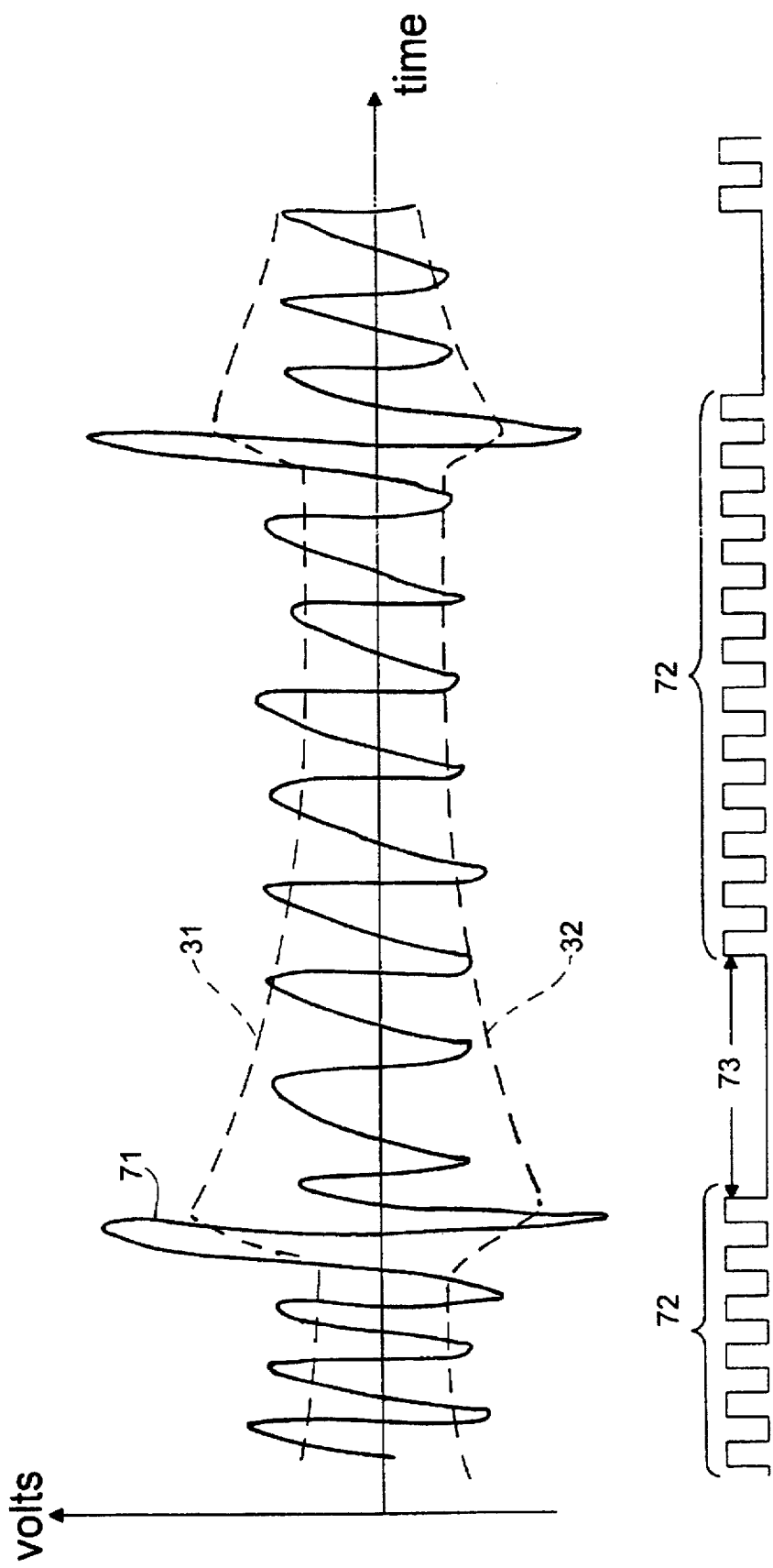
FIG. 7 shows details of the operation of the noise detector with high amplitude noise.
Figure 8:
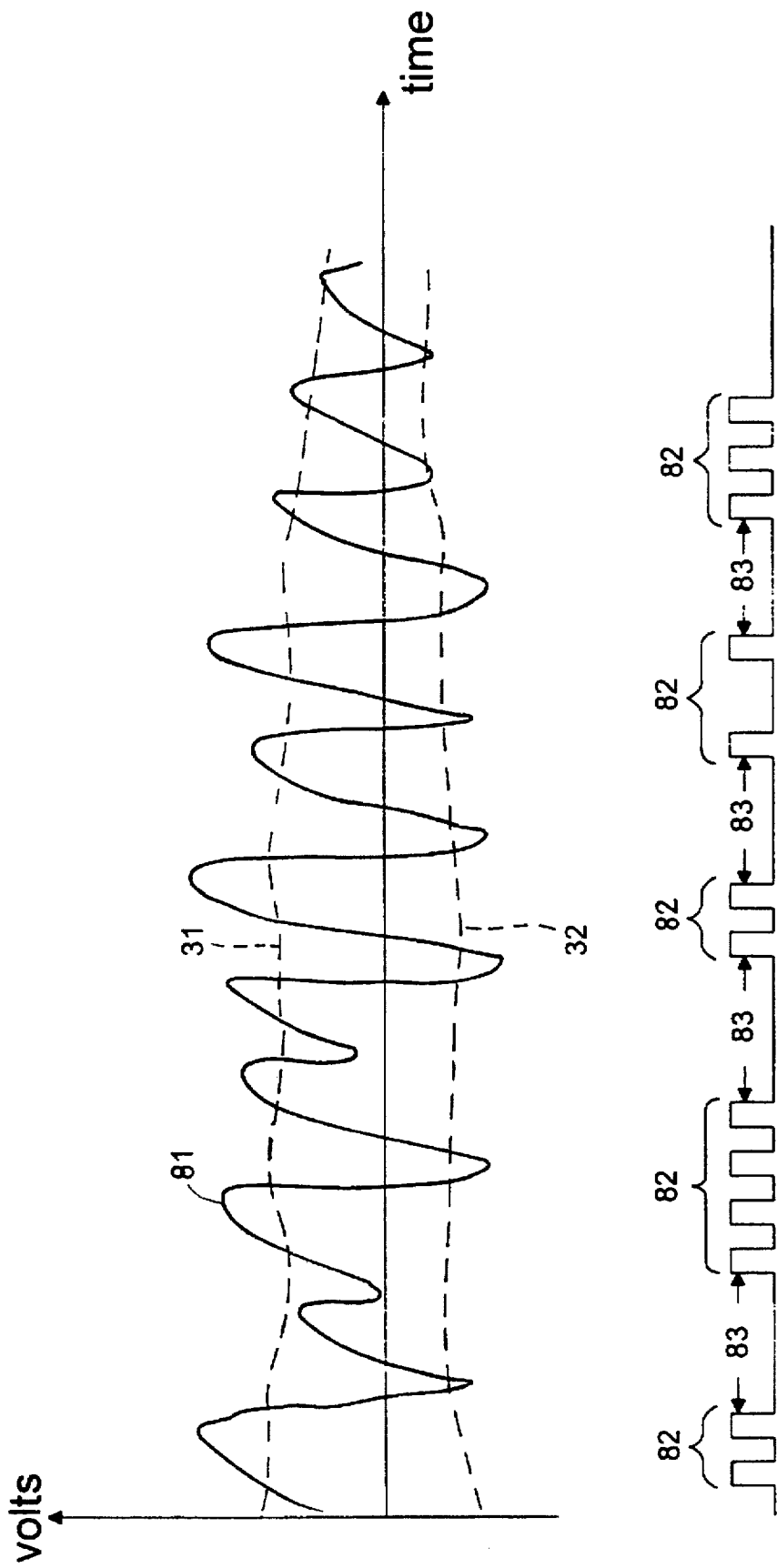
FIG. 8 shows details of the operation of the noise detector with ventricular fibrillation.

These principles are illustrated in FIGS. 6–8. In each of these Figures the top trace indicates a particular IECG together with the thresholds 31 and 32 as defined above. The bottom trace in each Figure shows the corresponding train pulses on line 102.

FIG. 6 shows a normal IECG trace 61 with a low amplitude noise component. As seen on the bottom trace of this Figure, each QRS complex results in a short train 62 of pulses separated by pulse intervals. In addition, the pulse trains are separated by idle periods 63. In general, each pulse of a train having pulse intervals below a certain minimum threshold level, of, for example 30 milliseconds, is recognized as a potential noise pulse trains and counted by counter 104. In addition, the idle period between the pulse trains is also monitored. In FIG. 6, the number of pulses on train 62 is too small to be counted as noise. In addition, idle period 63 is relatively, long, exceeding the noise detection interval 73, (TDI) while interval 83 in shorter than interval 73. The counter is reset to zero and no 'Noise' output signal is generated. Accordingly, the detector 27 makes the decision that the ICEG is not contaminated with noise and that normal operation can proceed.

In FIG. 7, IECG 71 consists of consecutive QRS complexes with a high amplitude noise component. As shown in the bottom trace of this Figure, the corresponding signal on line 102 consists of long trains of pulses separated by short intervals (below 30 ms). The train pulses 72 are separated by a idle period 73. The idle period 73 is consistent with the short delays between QRS complexes associated with tachycardia and could be misclassified as such by controller 15. However, the long pulse trains 72 (consisting of example of over 20 pulses each) indicate, in fact, that the IECG signal 71 has a high amplitude noise component. Therefore the analyzer generates a NOISE signal 28 to indicate to the controller 15 that the ICEG is too contaminated with noise for reliable identification of tachycardia, and thus the device should not deliver any therapy for any tachycardia that may be indicated by the tachycardia detector.

Finally, in FIG. 8, the IECG 81 consists of closely spaced QRS signals indicative of tachycardia. The corresponding signal on line 102 consists of very short pulse trains 82 separated by short idle periods 83. Since both the number of pulses in each train 82 and the idle period 83 are low, the analyzer does not generate a NOISE signal. Accordingly, the controller can proceed with antitachycardia or defibrillation therapy.

Thus this invention provides a more accurate and reliable classification of noise, and the embodiment disclosed herein describes a system that uses dual detectors with dual independent thresholds. It can be seen that this method of noise detection is applicable to systems which have a single adaptive threshold. The key requirement of this method lies in the detector having a very short refractory period so that a large number of noise intervals are capable of being detected and that noise is classified when a number (15 to 30) of consecutive very short 'noise' intervals are counted.

Although the invention has been described with reference to a preferred embodiment, it is to be understood that this embodiment is merely illustrative of the application of the principles of the invention. Accordingly, the embodiment described in particular should be considered exemplary, not limiting, with respect to the following claims.

I claim:

1. An implantable cardiac device comprising:

means for sensing cardiac activity from a patient's heart to generate an input signal;

means for generating pacing signals for said heart;

means for defining a range for said input signal, said means for defining said range including means for changing said range dynamically in response to changes in the magnitude of said input signal;

means for processing said input signal to generate raw sense signals indicative excursions of said input outside said range;

means for generating a noise indication signal based on said raw sense signals to indicate that said input signal has a large noise component; and means for controlling said means for generating said pacing signals based on said noise signal.

2. The device of claim 1 wherein said means for generating said noise indication signal includes means for combining said raw signals to generate consecutive trains of pulses.

3. The device of claim 2 wherein said means of generating said noise indication signal includes means for sensing the number of pulses in each train and an idle period between each said train.

4. The device of claim 3 wherein said means of generating said noise indication signal includes means for sensing the number of said pulses and counting the number of pulses that have pulse intervals which are shorter than a predetermined interval.

5. An implantable cardiac device for treating or monitoring normal and malignant heart rhythms comprising:

means for sensing cardiac electrical activity from a patient's heart;

means for amplifying and filtering said signals to define a QRS complex;

means for detecting said QRS complex by when said signal crosses a voltage threshold;

means for measuring a time interval between successive said detects;

means for identifying a malignant heart rhythm from said time intervals;

means for counting a number of consecutive detect intervals that are shorter than a pre-selected threshold, said threshold being indicative of sensed signals which have a non-physiological origin and indicate a presence of noise contamination;

means for providing a noise indication when a said number of consecutive short detect intervals exceeds a pre-determined value; and means for detecting an idle period between said consecutive detects, wherein said noise indication is provided if said idle period is below a pre-selected threshold.

6. The device of claim 5 further comprising a disabling means for disabling said means for identifying said heart rhythm in the presence of noise contamination to prevent an erroneous tachycardia identification.

7. The device of claim 5 further comprising means for dynamically adjusting said voltage threshold for an optimal detection of said QRS complex.

8. The device of claim 7 wherein said means for adjusting said threshold includes means for sensing an amplitude of said QRS complex and means for changing said threshold in accordance with said amplitude.

9. The device of claim 5 wherein said means for detecting said QRS complex includes means for detecting when said signal exceeds a first threshold voltage to generate first pulses and means for detecting when said signal exceeds a second threshold voltage to generate second pulses.

10. The device of claim 9 wherein said detecting means further includes combining means for combining said first and second pulses into consecutive train pulses.

11. An implantable cardiac device for treating or monitoring normal and malignant heart rhythms comprising:

means for sensing cardiac electrical activity from a patient's heart;

means for amplifying and filtering said signals to define a QRs complex;

means for detecting said QRS complex by when said signal crosses a voltage threshold;

means for dynamically adjusting said voltage threshold for an optimal detection of said QRS complex;

means for measuring a time interval between successive said detects;

means for identifying a malignant heart rhythm from said time intervals;

means for counting a number of consecutive detect intervals that are shorter than a pre-selected threshold, said threshold being indicative of sensed signals which have a non-physiological origin and indicate a presence of noise contamination; and means for providing a noise indication when a said number of consecutive short detect intervals exceeds a pre-determined value.

* * * * *